US009738852B2

(12) United States Patent
Wang et al.

(10) Patent No.: US 9,738,852 B2
(45) Date of Patent: Aug. 22, 2017

(54) METHOD OF SEPARATING OIL

(71) Applicant: Croda, Inc., Edison, NJ (US)

(72) Inventors: Min Ma Wang, Kennett Square, PA (US); Craig Michael Sungail, Chadds Ford, PA (US); Xin Chen, Hockessin, DE (US)

(73) Assignee: Croda, Inc., Edison, NJ (US)

( * ) Notice: Subject to any disclaimer, the term of this patent is extended or adjusted under 35 U.S.C. 154(b) by 0 days.

(21) Appl. No.: 15/030,210

(22) PCT Filed: Jan. 8, 2016

(86) PCT No.: PCT/US2016/012583
§ 371 (c)(1),
(2) Date: Apr. 18, 2016

(87) PCT Pub. No.: WO2016/114982
PCT Pub. Date: Jul. 21, 2016

(65) Prior Publication Data
US 2016/0355750 A1    Dec. 8, 2016

Related U.S. Application Data

(60) Provisional application No. 62/104,174, filed on Jan. 16, 2015.

(51) Int. Cl.
*C11B 3/00*        (2006.01)
*C11B 13/00*       (2006.01)
*C07C 69/52*       (2006.01)
*C07C 69/33*       (2006.01)

(52) U.S. Cl.
CPC .............. *C11B 3/006* (2013.01); *C07C 69/33* (2013.01); *C07C 69/52* (2013.01); *C11B 13/00* (2013.01); *Y02W 30/74* (2015.05)

(58) Field of Classification Search
CPC ....................................................... C11B 3/006
USPC ....................................................... 554/212
See application file for complete search history.

(56) References Cited

U.S. PATENT DOCUMENTS

| 4,702,798 | A | 10/1987 | Bonanno |
| 6,268,010 | B1 | 7/2001 | Sekula |
| 6,566,305 | B1 * | 5/2003 | Milius ............... A01N 25/02 |
| | | | 504/116.1 |
| 7,497,955 | B2 | 3/2009 | Scheimann |
| 8,841,469 | B2 | 9/2014 | Shepperd |
| 8,962,059 | B1 | 2/2015 | Froderman |
| 9,090,851 | B2 | 7/2015 | Blankenburg |
| 9,255,239 | B1 | 2/2016 | Wiese |
| 2012/0245370 | A1 * | 9/2012 | Sheppard ............ C11B 1/10 |
| | | | 554/204 |
| 2014/0155639 | A1 | 6/2014 | Sticklen |
| 2014/0171670 | A1 | 6/2014 | Jenkins |
| 2015/0184112 | A1 | 7/2015 | Lewis |
| 2015/0284659 | A1 | 10/2015 | Young |

FOREIGN PATENT DOCUMENTS

| WO | 2012128858 | 9/2012 | |
| WO | 2013041876 | 3/2013 | |
| WO | WO 2013041876 A1 * | 3/2013 | ........... B01D 17/047 |
| WO | 2015057191 | 4/2015 | |

OTHER PUBLICATIONS

International Search Report and Written Opinion of the International Searching Authority for International Application No. PCT/US2016/012583 dated Aug. 5, 2016, 10 pages.
Non Final Office Action for U.S. Appl. No. 15/423,838, dated Mar. 23, 2017, 6 pages.
U.S. Notice of Allowance for U.S. Appl. No. 15/145,085, dated Feb. 27, 2017, 11 pages.
Final Office Action for U.S. Appl. No. 15/145,085, dated Nov. 9, 2016, 16 pages.

* cited by examiner

*Primary Examiner* — Deborah D Carr
(74) *Attorney, Agent, or Firm* — RatnerPrestia

(57) ABSTRACT

A method of separating oil from a composition containing an oil and water emulsion, by adding a separation additive which is a fatty ester of alkoxylated glycerol, and performing at least one oil separation step. The method is particularly suitable for separating corn oil from stillage produced in a corn ethanol mill.

13 Claims, No Drawings

US 9,738,852 B2

METHOD OF SEPARATING OIL

This application is the U.S. national phase filing under 35 U.S.C. §371 of International Application No. PCT/US2016/012583, filed on 8 Jan. 2016, and claims the benefit of priority of, U.S. Provisional Application No. 62/104,174, entitled METHOD OF SEPARATING OIL, filed on 16 Jan. 2015, the contents of which are incorporated herein by reference in their entirety for all purposes.

FIELD OF INVENTION

The present invention relates to a method of separating oil from an emulsion containing composition, preferably a biomass, particularly stillage, using a separation additive which is an alkoxylated ester.

BACKGROUND

There is growing interest in the use of bioethanol to supplement fossil fuels as an energy source in transport. For example, ethanol accounted for 9% of gasoline consumption in the USA in 2009, and 90% of the ethanol produced in the USA in 2009 was produced using corn as feedstock. The majority of existing corn ethanol mills, and almost exclusively all the corn ethanol mills commissioned in recent years, are so called "dry mills".

A "dry mill" plant processes corn into ethanol through a dry grinding process. The ground corn is mixed with water to form mash, and then an enzyme is added to convert corn starch into sugar. A fermentation process is followed to convert the sugar into ethanol. The liquid intermediate, called "beer," is further processed by distillation and ethanol is collected. The leftover in the "beer" after the removal of ethanol is called stillage, which contains water, protein, nutrients, fibre, and corn oil. The stillage includes an aqueous phase and an oil phase. The corn oil may be separated from the stillage by using a centrifuge and collected as a higher value co-product. A separation additive may be added into the stillage to enhance the separation of the oil phase from the water phase and increase the corn oil yield. Ethanol plants may treat whole stillage from the "beer" column via centrifugation to produce wet cake and thin stillage, and further treat the thin stillage stream by subjecting it to multiple effect evaporation to increase the solids content and recover the distillate for return use in the process. As the solids content increases, the thin stillage is typically referred to as syrup. The syrup is typically combined with wet cake or distillers' dry grains (DDG) and sold as animal feed.

The corn oil yield from a stillage depends on many factors, such as corn kernel quality, water content, the particle size of the solids in the stillage, the process temperature of the stillage in the centrifuge, and the design of the separation equipment. The use of a corn oil separation additive is intended to increase the corn oil yield.

WO2012/128858 of Hercules Incorporated discloses the use of polyoxyethylene(20) sorbitan mono-laurate (polysorbate 20), polyoxyethylene(20)sorbitan mono-stearate (polysorbate 60) and polyoxyethylene(20)sorbitan mono-oleate (polysorbate 80) as corn oil separation additives. The specific additives disclosed in WO2012/128858 are all based on sorbitan and although the yield of corn oil obtained from stillage in the presence of such additives is improved, there can still be a significant amount of corn oil left un-collected, and discharged unseparated from the stillage as part of a product with lower commercial value. The composition of the stillage can vary considerably as can the effectiveness of the sorbitan derivatives as oil separation aids with different stillages. There is a need for alternative or improved separation additives which are also effective with a wide range of stillages.

The present invention seeks to aid the recovery of oil from a wide range of aqueous compositions, particularly from different biomass materials, and especially from different stillages.

SUMMARY OF THE INVENTION

We have surprisingly discovered a method of separating or recovering oil which overcomes or significantly reduces at least one of the aforementioned problems. Accordingly, the present invention provides a method of separating oil from a composition comprising an oil and water emulsion, which comprises adding a separation additive to the composition and performing at least one oil separation step, wherein the separation additive comprises a fatty ester of alkoxylated glycerol. The invention also provides a stillage and product derived therefrom comprising a fatty ester of alkoxylated glycerol.

The invention further provides a separation additive comprising a fatty ester of alkoxylated glycerol obtainable by alkoxylating a mixture of a triglyceride and glycerol.

The invention yet further provides the use of a separation additive comprising a fatty ester of alkoxylated glycerol to separate oil from stillage.

All of the features described herein may be combined with any of the above aspects of the invention, in any combination.

The oil containing composition is suitably a biomass, by which is generally meant organic matter harvested or collected from a biological source. The biological source is preferably renewable and includes plant materials (e.g. plant biomass), animal materials, microbial materials such as bacteria, fungi and algae, and/or materials produced biologically. The biomass will normally contain glycerides (e.g. tri-, di-, and/or mono-glyceride).

In one preferred embodiment, the composition or biomass is stillage, by which is meant a co-product or by-product produced during production of a biofuel, particularly when using corn as feedstock. The term "stillage" can refer to whole stillage, thin stillage, or concentrated stillage such as condensed distillers soluble, i.e. syrup, which can be produced from biofuel process streams, e.g. bioethanol production process streams.

The fatty component of the fatty ester of alkoxylated glycerol is generally derived from fatty acids or derivatives thereof. Preferably, the fatty ester is derived from fatty acids and/or derivatives thereof. The fatty acids are preferably mono-carboxylic acids and may be linear and/or branched, saturated and/or unsaturated. Unsaturated fatty acids are preferred. The unsaturated fatty acids may be mono-unsaturated, di-unsaturated and/or poly-unsaturated. Linear fatty acids are preferred.

The fatty acids suitably have at least 6 carbon atoms, preferably at least 10 carbon atoms, more preferably at least 12 carbon atoms, particularly at least 14 carbon atoms, and especially at least 16 carbon atoms. The fatty acids preferably have at most 24 carbon atoms, more preferably at most 22 carbon atoms, and particularly at most 20 carbon atoms. Preferably the fatty acids have in the range from 6 to 24, more preferably 14 to 22, and particularly 16 to 20 carbon atoms.

Suitable saturated fatty acids may be selected from the group consisting of hexanoic (caproic), octanoic (caprylic), nonanoic, decanoic (capric), undecanoic, dodecanoic (lauric), tridecanoic, tetradecanoic (myristic), 2-ethyl hexanoic, trimethylhexanoic, trimethylnonanoic, hexadecanoic (palmitic), octadecanoic (stearic), isostearic, decadecanoic, acids and mixtures thereof. Suitable unsaturated fatty acids may be selected from the group consisting of oleic, ricinoleic, linoleic, linolenic, acids and mixtures thereof. The unsaturated fatty acids may be selected from the group consisting of oleic acid, linoleic acid and mixtures thereof. Oleic acid is a preferred unsaturated fatty acid.

The fatty acids are preferably mixtures obtained from natural sources, such as, for example, plant or animal esters, particularly triglycerides. Fatty acids derived from plant sources are preferred. Suitable natural sources include those selected from the group consisting of canola oil, soya bean oil, corn oil, tall oil, palm kernel oil, coconut oil, rapeseed oil, high erucic rapeseed oil, tallow oil and mixtures thereof. Soya bean fatty acids are particularly preferred. Preferably, the fatty acids are selected from the group consisting of canola, soya bean, corn, tall, palm kernel, coconut, rapeseed, high erucic rapeseed, tallow fatty acids and mixtures thereof.

In one preferred embodiment, the fatty component of the fatty ester of alkoxylated glycerol is derived from fatty acids, particularly comprising, consisting essentially of, or consisting of, soya bean fatty acids.

The fatty ester of alkoxylated glycerol is preferably a partial ester, i.e. preferably not fully esterified.

The fatty ester of alkoxylated glycerol preferably comprises on average less than 3 ester bonds or fatty chains (e.g. fatty acid residues). The fatty ester of alkoxylated glycerol suitably comprises on average in the range from 1.0 to 2.5, preferably 1.0 to 2.0, more preferably 1.0 to 1.5, particularly 1.0 to 1.2, and especially 1.0 to 1.1 ester bonds (or fatty chains).

The alkylene oxide groups of the fatty ester of alkoxylated glycerol are typically present as polyalkylene oxide chains of the formula: $-(C_rH_{2r}O)_n-$ where n is the number of alkylene oxide groups in the chain, r is 2, 3 or 4, preferably 2 or 3, i.e. an ethyleneoxy ($-C_2H_4O-$) or propyleneoxy ($-C_3H_6O-$) group. Preferably the fatty ester of alkoxylated glycerol comprises a polyalkylene oxide chain. There may be different alkylene oxide groups along the polyalkylene oxide chains. Preferably, it is desirable that the chain is a homopolymeric ethylene oxide chain. However, the chain may be a homopolymeric chain of propylene oxide residues or a block or random copolymer chain containing both ethylene oxide and propylene oxide residues. Where co-polymeric chains of ethylene and propylene oxide units are used, the molar proportion of ethylene oxide units used is suitably at least 50 mol %, preferably at least 70 mol %, more preferably at least 80 mol %, and particularly at least 90 mol %. The average number of alkylene oxide groups in the polyalkylene oxide chains of the fatty ester of alkoxylated glycerol, i.e. the value of the each parameter n, is suitably in the range from 1 to 20, preferably 3 to 10, more preferably 4 to 7, particularly 4.5 to 6.5, and especially 5 to 6. The value of the index n is an average value, which includes statistical variation in the chain length.

The total number of alkylene oxide, preferably ethylene oxide, groups in the polyalkylene oxide chains of the fatty ester of alkoxylated glycerol (i.e. the average number of alkylene oxide groups in each chains (parameter n)×the number of chains) is suitably in the range from 6 to 40, preferably 12 to 30, more preferably 14 to 20, particularly 15 to 19, and especially 16 to 18.

The fatty ester of alkoxylated glycerol used herein may be produced in a conventional manner, for example by firstly alkoxylating glycerol, by techniques well known in the art, for example by reacting with the required amounts of alkylene oxide, for example ethylene oxide and/or propylene oxide. The second stage of the process may comprise reacting the alkoxylated glycerol residue with a fatty acid or a derivative thereof. The direct reaction between the fatty acid and the alkoxylated glycerol can be carried out, with or without catalysts, by heating preferably to a temperature of greater than 100° C., more preferably in the range from 200 to 250° C. Synthesis using reactive derivatives will usually be possible under milder conditions, for example using lower fatty acid esters, fatty acid chlorides and/or their respective anhydrides. Purification of the reaction product is not usually necessary, but can be carried out if desired.

Generally the alkoxylation reaction will replace all of the active hydrogen atoms in the glycerol molecule. However, reaction at a particular site may be restricted or prevented by steric hindrance or suitable protection. The terminating hydroxyl groups of the polyalkylene oxide chains in the resulting compounds are then available for reaction with acyl compounds to form ester linkages.

In one preferred embodiment, the fatty ester of alkoxylated glycerol is produced in a transesterification/alkoxylation process, more preferably when using a triglyceride and glycerol as starting material. Preferably, the separation additive is obtainable by alkoxylating a mixture of a triglyceride and glycerol. The triglyceride (e.g. soya bean oil) and glycerol can be charged into a reactor vessel together with a base catalyst (such as NaOH or KOH, normally in aqueous solution at 40 to 50% active levels). With agitation on, the reaction vessel is preferably heated to about 100° C. and a vacuum applied to remove water. After purging with nitrogen, the reaction vessel is preferably heated to about 140° C., and alkylene oxide, for example ethylene oxide and/or propylene oxide, gradually introduced into the reaction vessel. The addition of alkylene, preferably ethylene, oxide may take from about 3 to 6 hours, and up to 20 hours to complete at 140 to 155° C. An additional 3 to 6 hours may be required to complete the reaction.

The method of producing the fatty ester of alkoxylated glycerol described herein can surprisingly result in a high purity product such that the separation additive used herein suitably comprises greater than 75 wt %, preferably in the range from 85 to 100 wt %, more preferably 90 to 99.9 wt %, particularly 95 to 99.5 wt %, and especially 97 to 99 wt % of fatty ester of alkoxylated glycerol, based on the total weight of the separation additive.

The separation additive may also comprise an amount of alkoxylated, preferably ethoxylated, fatty ester which may be formed during the synthesis of fatty ester of alkoxylated glycerol. The alkoxylated fatty ester may be a mono-ester, di-ester or a mixture thereof.

The separation additive composition preferably comprises in the range from 0 to 10 wt %, more preferably 0 to 5 wt %, particularly 0.05 to 2 wt %, and particularly 0.1 to 1 wt % of alkoxylated fatty ester, based on the total weight of the separation additive.

The separation additive may also comprise an amount of alkoxylated, preferably ethoxylated, glycerol. The separation additive composition preferably comprises in the range from 0 to 8 wt %, more preferably 0 to 4 wt %, particularly 0.05 to 2 wt %, and particularly 0.1 to 1 wt % of alkoxylated glycerol, based on the total weight of the separation additive.

The separation additive composition may also comprise an amount of polyalkylene, preferably polyethylene, oxide. The separation additive preferably comprises in the range from 0 to 8 wt %, more preferably 0 to 4 wt %, particularly 0 to 2 wt %, and particularly 0 to 0.5 wt % of polyalkylene oxide, based on the total weight of the separation additive.

The separation additive preferably has a hydroxyl value (measured as described herein) in the range from 60 to 110, more preferably 70 to 100, particularly 80 to 90, and especially 83 to 87 mgKOH/g, an acid value (measured as described herein) preferably less than 3, more preferably less than 1, particularly less than 0.5, and especially less than 0.1 mgKOH/g, and/or a saponification value (measured as described herein) in the range from 30 to 100, more preferably 40 to 75, particularly 45 to 60, and especially 50 to 55 mgKOH/g.

The separation additive suitably has a HLB value (calculated using Griffin's method as is well known in the art) in the range from 11 to 16, preferably 12 to 15, more preferably 13 to 14, particularly 13.2 to 13.6, and especially 13.3 to 13.5. The separation additive is preferably liquid at 25° C., more preferably also liquid at 20° C., particularly also liquid at 15° C., and especially also liquid at 10° C. Preferably the separation additive is acceptable for animal consumption. This may be required because the composition treated with the separation additive and/or the separated components thereof may be used for animal consumption. For example, treated stillage may be used in the production of distillers' dried grains (DDG) or distillers' dried grains with solubles (DDGS). DDG or DDGS may be used as an animal feedstock. Preferably the separation additive is acceptable for animal consumption. The separation additive may be generally recognized as safe (GRAS). The requirement that the separation additive is acceptable for animal consumption may also influence the concentration of additive which may be added to the composition, preferably stillage. This is because there will typically be an upper concentration limit specified for the presence of the separation additive in the animal feedstock so that it is acceptable for animal consumption. This upper concentration limit may determine the maximum concentration of separation additive which may be added to the stillage. For GRAS, the maximum concentration of separation additive which may be added to the composition may be 1,000 ppm by weight. If the maximum concentration of separation additive in the composition is determined by the presence of the additive in the animal feedstock then an additive with a higher separation performance will be preferred to increase the oil yield.

The separation additive may be added to the composition, preferably stillage at a dosage of at most 4,000 parts per million (ppm) of separation additive based on the weight of the composition. The separation additive may be added at a dosage of at most 3,000 ppm, preferably at most 2,000 ppm, more preferably at most 1,500 ppm, particularly at most 1,000 ppm, and especially at most 800 ppm. The separation additive may be added at a dosage of at least 50 ppm, preferably at least 100 ppm, more preferably at least 200 ppm, and particularly at least 300 ppm.

The separation additive may be added at a dosage of at most 1,000 ppm to satisfy the requirements to be GRAS. Preferably the separation additive is added at a dosage rate of at least 50 ppm and at most 1,000 ppm based on the weight of the composition, preferably stillage.

In general, the process steps in ethanol production which include the distillation which separates ethanol from the whole stillage and the further downstream process steps are known as 'back-end' process steps. A typical process flow for the back-end process steps may include:
1. Distillation to separate ethanol from the whole stillage;
2. Centrifugation of the whole stillage to produce thin stillage and wet cake;
3. Evaporation of the thin stillage to produce steam and syrup (dewatered thin stillage); and
4. Drying of the syrup to produce DDGS.

The ethanol production process may be a Delta T or ICM corn to ethanol production process.

The method of the present invention may be used with whole stillage, thin stillage or syrup. Preferably the separation additive is added to a whole stillage or a thin stillage. The stillage typically comprises fibre, protein, lipids and yeast. The oil phase of the stillage may include triglycerides.

The separation operation in the method of the invention may comprise one or more of a centrifugation operation, evaporation operation and drying operation.

Preferably, the separation operation includes centrifugation, and the separation additive is added to the stillage before or during centrifugation. Preferably, the separation additive is added to the stillage before the centrifugation occurs. The separation additive may be added after the majority of ethanol has been distilled away and before centrifugation.

Centrifugation may occur for at least one minute, preferably at least two minutes, more preferably at least 3 minutes. Centrifugation may occur for up to 15 minutes, preferably up to 10 minutes, more preferably up to 6 minutes.

The time between the separation additive being added to the stillage and the oil phase being separated from the stillage may be at least thirty seconds, preferably at least one minute, more preferably at least two minutes, and particularly at least 3 minutes. The time between the separation additive being added to the stillage and the oil phase being separated from the stillage may be up to 24 hours, preferably up to 12 hours, more preferably up to 4 hours, and particularly up to 1 hour. The time between the separation additive being added to the stillage and the oil phase being separated from the stillage may be up to 45 minutes, preferably up to 30 minutes, more preferably up to 15 minutes, and particularly up to 10 minutes.

The method according to the present invention may be performed above room temperature. The method may be performed at a temperature of at least 30° C., preferably at least 50° C., more preferably at least 70° C. The method may be performed at a temperature of at most 95° C., preferably at most 90° C. If the method is performed at a higher temperature, the oil phase and water phase of the composition may separate more quickly. The separation additive may advantageously lower the temperature required to achieve a predetermined amount of separation by increasing the amount of the oil phase which is separated in a predetermined time without requiring a higher temperature. This may reduce the amount of heat energy (and therefore cost) required for the separation operation.

The method of the present invention may increase the amount of the oil phase separated from the composition, preferably stillage, when compared with a separation method in which no separation additive is used. The separation of an increased amount of the oil phase from the stillage may improve the corn oil yield of the process. The separation of an increased amount of the oil phase from the stillage may also reduce the amount of oily deposits on stillage process equipment downstream of the separation. This may reduce the need for cleaning of the equipment and so may reduce the amount of downtime required to maintain the equipment.

In addition, the oil, preferably corn oil, recovered using the method of the present invention may be of improved quality. The oil recovered may have a lower solids content or a lower water content than oil recovered without using the separation additive of the present invention.

As shown in the examples below, the separation additive may perform better than an equivalent amount by weight of polysorbate 80. Better performance in this context should be understood to mean that more of the oil phase is separated by the separation additive from an equivalent amount of stillage under an equivalent separation operation than is separated by an equivalent amount by weight of polysorbate 80.

A predetermined amount of the separation additive may enable at least 10% more of the oil phase to be separated from a composition, preferably stillage, than an equivalent amount by weight of polysorbate 80 under equivalent separation conditions. Preferably the separation additive may enable at least 15% more of the oil phase to be separated from the composition, preferably stillage, than an equivalent amount by weight of polysorbate 80, more preferably at least 20% more, and particularly at least 30% more. The separation additive may enable at most 100% more of the oil phase to be separated than an equivalent amount by weight of polysorbate 80, preferably at most 90% more, more preferably at most 70% more. The increase in oil phase separation may be measured by volume.

The predetermined amount may be at most 1,000 ppm, preferably is 400 ppm, of separation additive based on the weight of the composition, preferably stillage.

All of the features described herein may be combined with any of the above aspects of the invention, in any combination. In addition, any upper or lower quantity or range limit used herein may be independently combined.

In this specification the following test methods were used:

i) Corn Oil Separation

Thin stillage samples obtained from corn ethanol plants were stored in a refrigerator to keep from being spoiled. Prior to the test, a stillage sample was taken out of the refrigerator and heated to 82° C. in an oven. 40 ml of the pre-heated stillage sample was added to a 50 ml centrifuge tube, and 400 ppm of separation additive was added into the sample. The sample was centrifuged at 7,000 rpm for 3 minutes. The height of the clear oil layer was measured (in mm) with a ruler.

ii) Acid Value

The acid value of the separation additive was determined by using ASTM D1980-87 (Standard test method for acid value of fatty acids and polymerised fatty acids).

iii) Hydroxyl Value

The hydroxyl value of the separation additive was measured by using ASTM D1957-86 (Standard test method for hydroxyl value of fatty oils and acids).

iv) Saponification Value

The saponification value of the separation additive was measured by using ASTM D5558 (Standard test method for vegetable and animal fats).

v) Chemical Composition

The chemical composition of the separation additive was determined by Maldi-MS. Three solutions were prepared. One contained the separation additive sample in chloroform at a volume concentration of 1%. The second contained dithranol, a common matrix used for MALDI mass spectrometry, dissolved in chloroform at a volume concentration of 1%. The third contained potassium bromide dissolved in methanol at a volume concentration of 1%. Portions of the three solutions were combined in volume ratios of 100 parts matrix solution, 20 parts sample solution, and 1 part potassium bromide solution. A one-microliter sample of this mixture was spotted onto a MALDI plate, upon which it dried immediately. The MALDI spectrum was acquired using a Bruker autoflex speed MALDI mass spectrometer, operated in reflector mode. Immediately prior to collection of the spectrum of the sample, the mass scale of the instrument was calibrated using a mixture of peptides provided by Bruker for this purpose. The spectrum was imported into the data analysis program Polymerix™ (Ver. 3.0.0) from Sierra Analytics, Inc. Peaks were assigned based on knowledge of the reaction chemistry and best fits to the data.

The invention is illustrated by the following non-limiting examples.

EXAMPLE 1

The fatty ester of alkoxylated glycerol was produced in a one pot process using the materials listed in Table 1.

TABLE 1

| Raw Material | Wt (g) | Molar Ratio | Wt. % |
|---|---|---|---|
| Glycerol | 90.2 | 1.86 | 6.4 |
| Soybean Oil (ex Cargill) | 462.8 | 1.0 | 33.1 |
| Ethylene Oxide | 847.0 | 36.5 | 60.5 |
| Sub-Total | 1400 | | 100.0 |
| KOH (45%) | 2.0 | | ~0.07 |
| H$_3$PO$_4$ | 2.0 | | |

Reaction Process:

i) The soya bean oil and catalyst (caustic potash, 45%) were added to a clean and dry 2-L pressurized Parr reactor at ambient temperature.

ii) The reactor was heated slowly to 100° C. with agitation and nitrogen sweep on.

iii) As the temperature was increased, vacuum was applied to remove water.

iv) Once the residual water was reduced to below 0.2% at temperature range of 90 to 100° C., the glycerol was added.

v) With agitation on, the reaction mixture was purged with nitrogen and the reactor temperature increased to 130° C.

vi) The ethylene oxide was fed into the reactor at the temperature range of 130 to 150° C. The ethylene oxide feeding rate was controlled so that the reactor pressure did not exceed 50 psig.

vii) Once all the ethylene oxide had been added, the reactor pressure was allowed to decrease at the reaction temperature range of 140 to 150° C. After the pressure drop reached a steady low rate, the reaction was continued for another 2 hours.

viii) Vacuum was gradually applied to 20 torr or less in order to remove any unreacted ethylene oxide. The reactor temperature and vacuum were held for another 1 to 2 hours.

iix) The reactor temperature was allowed to cool to 60 to 65° C., the product was neutralized with phosphoric acid, and the reaction product was then discharged. The reaction product had an acid value of 0.07 mg KOH/g, a hydroxyl value of 85.2 mg KOH/g and a saponification value of 52.9 mg KOH/g.

EXAMPLE 2

The product produced in Example 1 was used as a separation additive in the corn oil separation test described herein using a stillage sample from a corn ethanol plant. The stillage was treated and the height of the clear oil layer (indicating the separation performance) was measured in millimeters (mm) for 5 samples. The average height was calculated. The results are shown in Table 2.

TABLE 2

| Sample No | 1 | 2 | 3 | 4 | 5 | Average (mm) |
|---|---|---|---|---|---|---|
| Stillage | 3 | 3 | 3 | 3 | 3 | 3 |

EXAMPLE 3

This is a Comparative Example not according to the invention. The procedure of Example 2 was repeated except that polysorbate 80 was used as the separation additive instead of the product produced in Example 1. The results are shown in Table 3.

TABLE 3

| Sample No | 1 | 2 | 3 | 4 | 5 | Average (mm) |
|---|---|---|---|---|---|---|
| Stillage | 2 | 2 | 2 | 2 | 2 | 2 |

The above examples illustrate the improved properties of the separation additive, and use thereof, according to the present invention.

It is to be understood that the invention is not to be limited to the details of the above embodiments, which are described by way of example only. Many variations are possible.

The invention claimed is:

1. A method of separating oil from a composition comprising an oil and water emulsion, which comprises adding a separation additive to the composition and performing at least one oil separation step, wherein the separation additive comprises a fatty ester of alkoxylated glycerol.

2. The method according to claim 1 wherein the fatty ester is derived from fatty acids and/or derivatives thereof.

3. The method according to claim 2 wherein the fatty acids are selected from the group consisting of canola, soya bean, corn, tall, palm kernel, coconut, rapeseed, high erucic rapeseed, tallow fatty acids and mixtures thereof.

4. The method according to claim 1 wherein the fatty ester of alkoxylated glycerol comprises 1.0 to 2.0 ester bonds.

5. The method according to claim 1 wherein the fatty ester of alkoxylated glycerol comprises a polyalkylene oxide chain and wherein the average number of alkylene oxide groups in each polyalkylene oxide chain of the fatty ester of alkoxylated glycerol is 4 to 7.

6. The method according to claim 5 wherein the total number of alkylene oxide groups in the polyalkylene oxide chains of the fatty ester of alkoxylated glycerol is 12 to 30.

7. The method according to claim 1 wherein the separation additive is obtainable by alkoxylating a mixture of a triglyceride and glycerol.

8. The method according to claim 1 wherein the separation additive comprises greater than 75 wt % of fatty ester of alkoxylated glycerol.

9. The method according to claim 8 wherein the separation additive comprises 90 to 99.9 wt % of fatty ester of alkoxylated glycerol.

10. The method according claim 1 wherein the separation additive has a HLB value of 13 to 14.

11. A stillage and product derived therefrom comprising a fatty ester of alkoxylated glycerol.

12. The stillage according to claim 11 wherein the fatty ester is derived from fatty acids and/or derivatives thereof.

13. The method according to claim 1 wherein the composition comprising an oil and water emulsion is stillage.

* * * * *